United States Patent [19]

Sutton et al.

[11] Patent Number: 5,155,021

[45] Date of Patent: Oct. 13, 1992

[54] METHOD AND KIT FOR DETERMINATION OF HERPES SIMPLEX VIRAL ANTIGEN BY DIRECT BINDING TO POLYMERIC PARTICLES

[75] Inventors: Richard C. Sutton; Thomas J. Cummins, both of Rochester; Nancy F. Green, Pittsford, all of N.Y.

[73] Assignee: Eastman Kodak Company, Rochester, N.Y.

[21] Appl. No.: 308,843

[22] Filed: Feb. 9, 1989

[51] Int. Cl.$^5$ ............... G01N 33/571; G01N 33/546
[52] U.S. Cl. .................... 435/5; 435/7.92; 435/7.95; 435/961; 435/975; 435/28; 436/531; 436/534; 436/174
[58] Field of Search ............ 435/5, 7.92, 7.95; 436/548, 510, 511, 533, 534, 518, 36, 531

[56] References Cited

U.S. PATENT DOCUMENTS

| | | | |
|---|---|---|---|
| 4,089,747 | 5/1978 | Bruschi | 435/10 |
| 4,430,437 | 2/1984 | Hampar et al. | 436/548 |
| 4,497,899 | 2/1985 | Armstrong et al. | 436/510 |
| 4,497,900 | 2/1985 | Abram et al. | 436/511 |
| 4,695,537 | 9/1987 | Dorsett | 435/5 |
| 4,828,978 | 5/1989 | Warren, III et al. | 435/5 |
| 4,847,199 | 7/1989 | Snyder et al. | 435/36 |
| 4,859,612 | 8/1989 | Cole et al. | 436/523 |
| 4,912,034 | 3/1990 | Kalra et al. | 435/7 |
| 5,030,561 | 7/1991 | Mapes et al. | 435/7.36 |

FOREIGN PATENT DOCUMENTS

| | | |
|---|---|---|
| 56-31646 | 3/1981 | Japan. |
| 86-02733 | 5/1986 | PCT Int'l Appl. |
| 87-03690 | 6/1987 | PCT Int'l Appl. |
| 2123146 | 9/1985 | United Kingdom. |

OTHER PUBLICATIONS

Rossier et al, "Microcarries in combination with enzyme immunofiltration and immunofluorescence for the detection of herpes simplex virus antigens in culture". J. Clin. Microbiol. vol. 21, No. 3, pp. 335–339 (Mar. 1985).

*Primary Examiner*—Esther L. Kepplinger
*Assistant Examiner*—Carol E. Bidwell
*Attorney, Agent, or Firm*—James L. Tucker

[57] ABSTRACT

Herpes simplex viral antigen can be readily determined by contacting a specimen containing Herpes simplex virus of herpes simplex viral-infected cells with polymeric particles which have a surface area of from about 0.1 to about 600 m$^2$/g. Within a few minutes of this contact, antigen which is bound to the particles is contacted with antibodies thereto so as to form an immunological complex on the particles. Bound complex is separated from uncomplexed materials, and the presence of the complex is then appropriately determined. A kit for determining herpes comprises the particles described above, a disposable test device having a microporous membrane and antibodies to herpes simplex viral antigen.

21 Claims, 1 Drawing Sheet

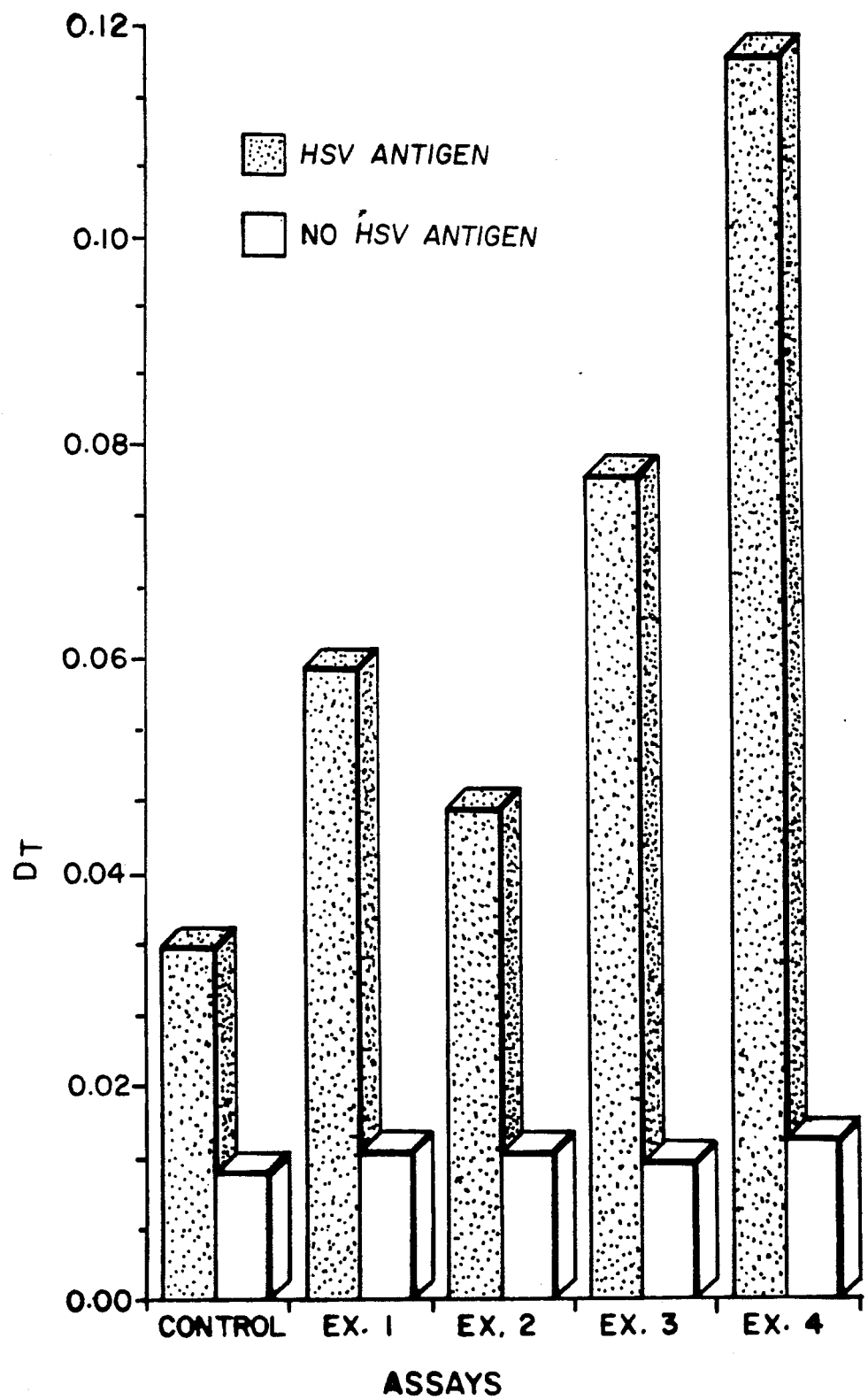

METHOD AND KIT FOR DETERMINATION OF HERPES SIMPLEX VIRAL ANTIGEN BY DIRECT BINDING TO POLYMERIC PARTICLES

FIELD OF THE INVENTION

This invention relates to a diagnostic test kit and method useful for the determination of Herpes simplex virus. More particularly, this invention determines herpes simplex viral antigen as an indication of the presence of the virus in a biological specimen using direct binding of antigen onto small polymeric particles.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is herpes simplex virus. Despite the increasing control of various viruses by vaccination or treatment with various anti-viral agents, infection by herpes simplex virus (identified herein as HSV) remains a serious problem. There are two types of HSV: type 1 which occurs mainly around the mouth, and type 2 which occurs primarily around the genital area of the human body. Skin infections and viral encephalitis are but two of the serious results from HSV infection.

Because of the widespread nature of herpes simplex viral infection, there is considerable interest in having a rapid, simple and reliable test for detection of the causative virus. However, there are several similar viruses which often are indistinguishable from HSV using known diagnostic procedures. Thus, a useful diagnostic test for HSV-1 or HSV-2 must be specific for these viruses only and must not be sensitive to viruses such as Epstein-Barr virus, cytomegalovirus, varicella zoster virus or any other flora.

Various methods have been developed to determine viruses including culture techniques, immunoelectrophoresis, enzyme linked immunosorbent assays (ELISA) and agglutination assays (see for example, U.S. Pat. Nos. 4,430,437 issued Feb. 7, 1984 to Hampar et al and 4,695,537 issued Sep. 22, 1987 to Dorsett).

There is a need in the art for an assay for directly detecting herpes simplex viral antigen on a solid support with the advantages of known methods, but with improved sensitivity and accuracy.

SUMMARY OF THE INVENTION

An improvement in the art is provided by a method for the determination of herpes simplex virus comprising:
A. contacting a specimen suspected of containing antigen extracted from herpes simplex virus with polymeric particles which have a surface area of from about 0.1 to about 600 m$^2$/g of particles, which particles are capable of having herpes viral antigen bound thereto,
B. within about 10 minutes of contacting step A, contacting herpes simplex viral antigen bound to the particles with antibody thereto so as to form an immunological complex on the particles,
C. separating the bound complex from uncomplexed materials, and
D. determining the presence of the complex as a measure of the presence of herpes simplex virus in the specimen.

The invention also provides a diagnostic kit useful for the determination of herpes simplex virus comprising:
a. polymeric particles which have a surface area of from about 0.1 to about 600 m$^2$/g of particles, which particles are capable of having herpes simplex viral antigen bound thereto,
b. a disposable test device comprising a microporous membrane which has an average pore size which prevents the particles having antigen bound thereto from passing through the membrane, and
c. antibodies directed to herpes simplex viral antigen.

The method of the present invention provides an effective, sensitive and accurate means for determination of the presence of HSV in test specimens. These advantages are possible because herpes simplex viral antigen, generally extracted from the virions, is directly "captured" (or bound) to small polymeric particles by either covalent means or adsorption. The bound antigen can then be complexed with appropriate antibodies and detected as a measure of the amount of virus in the specimen.

The polymeric particles provide improved sensitivity because of the amount of surface area available for antigen capture. That is, the particles provide from about 0.1 to about 600 m$^2$ surface area per gram of particles. In preferred embodiments, the particles are used in combination with a microporous membrane which retains the particles while allowing uncomplexed materials and fluid to drain through. Antigen may be bound to both the particles and the membrane in such instances.

BRIEF DESCRIPTION OF THE DRAWING

The FIGURE is a bar graph illustrating the results from the comparison assays described in Examples 1–4 below. The graph shows the resulting dye densities (D$_T$) for assays performed with antigen capture on various polymeric particles (0.2 weight % solids) and on a microporous membrane.

DETAILED DESCRIPTION OF THE INVENTION

Herpes simplex virus present in biological specimens can be detected by the present invention. Biological specimens can be obtained from a patient using standard medical and microbiological techniques. Biological specimens include, for example, swab specimens obtained from the cervix, urethra, eyes, throat or anus of a patient, and body fluids such as synovial fluid or fluid from lesions. The biological specimens so obtained are suspected of containing HSV or HSV-infected cells which comprise the antigens to be determined.

This invention can be used to detect intact viruses or extracted viral antigens. Moreover, whole virus-infected cells or membranes can be lysed to release virions or antigens thereof. It is advantageous that the virus be effectively lysed and sufficient antigen extracted to provide a sensitive assay in a relatively short period of time.

The antigens detectable with the present invention are present in either HSV-1 or HSV-2 or both strains. Glycoproteins are preferably extracted and detected with the present invention.

Antigen extraction can be accomplished using any suitable technique including physical disruption of the organisms by sonication, heating or centrifugation. Chemical extraction compositions have also been developed which utilize nonionic or anionic surfactants (see for example U.S. Pat. No. 4,661,349 issued Apr. 28, 1987 to Kino et al and U.S. Pat. No. 4,430,437, noted above).

A preferred extraction composition and procedure is described and claimed in U.S. Pat. No. 5,081,010 (issued Jan. 14, 1992 to Cummins, Sullivan, Madsen and Green and entitled "Extraction Composition, Test Kit and Their Use to Extract or Determine a Herpes Simplex Viral Antigen").

In general, it has a pH of from about 8.5 to about 12, and comprises one or more alcoholamines or salts thereof in an amount of at least about 0.05, and preferably from about 0.1 to about 1, molar. Useful alcoholamines include ethanolamine, diethanolamine, propanolamine, triethanolamine and salts thereof (such as hydrochlorides, sulfates, acetates, picrates and oxalates). Others would be readily apparent to one skilled in the art. Mixtures of alcoholamines or salts thereof can be used if desired.

The composition also includes one or more nonionic surfactants which are condensation products of an alkylphenol and ethylene oxide. Preferred alkylphenols have from 1 to 20 carbons in the linear or branched alkyl group on the phenol. Octylphenol is most preferred. Generally, these compounds have from 5 to about 35 ethylene oxide groups.

Other useful nonionic surfactants include, but are not limited to, polyoxyethylene ethers such as those sold under the TRITON TM mark (Rohm and Haas), for example TRITON TM X-100 and Triton TM N101, or under the BRIJ tradename (ICI Americas, Inc.), polyoxyethylenesorbitan derivatives, such as those sold under the TWEEN tradename (for example TWEEN 20" by ICI Americas, Inc.), and polyglycol ethers such as those sold under the TERGITOL tradename (for example TERGITOL NPX and NP-7, Union Carbide). Other useful materials would be readily apparent to one skilled in the art, especially after consulting the standard reference for surfactants, *McCutcheon's Emulsifiers and Detergents*, 1986 Edition, McCutcheon Division, Publishing Co., Glen Rock, N.J.

A third critical component of the extraction composition is one or more of cholic acid, a salt or derivative thereof. Useful materials include, but are not limited to, cholic acid, chenodeoxycholic acid, deoxycholic acid, sodium deoxycholate, potassium chenodeoxycholate, ammonium cholate and others readily apparent to one skilled in the art.

The extraction composition also includes an anionic surfactant. Useful anionic surfactants include, but are not limited to, water soluble or dispersible compounds comprising an alkyl sulfate anion and an alkali metal (for example, lithium, sodium or potassium) or ammonium cation, the alkyl having from about 6 to 20 carbon atoms. Preferably, the alkyl has from 6 to 12 carbon atoms (such as linear or branched hexyl, octyl, decyl, 2-methylhexyl and dodecyl groups). Arylsulfonic acids or salts thereof (as described above) having from 6 to 10 carbon atoms in the aryl nucleus would also be useful. Representative anionic surfactants include ammonium dodecyl sulfate, sodium dodecyl sulfate, rubidium dodecyl sulfate, sodium dodecyl sulfate, lithium hexyl sulfate, potassium octyl sulfate and lithium decyl sulfate.

An important optional component of the extraction composition is one or more inorganic salts, such as alkali metal, ammonium or alkaline earth salts. Representative salts include, but are not limited to, sodium chloride (which is most preferred), potassium chloride, ammonium chloride, calcium chloride, ammonium sulfate, barium sulfate and others readily apparent to one skilled in the art.

Extraction can be carried out by providing a biological specimen suspected of containing HSV or HSV-infected cells and extracting antigen in a suitable manner for the assay. Generally, the extraction procedure takes less than 10 minutes although a longer time may be desired with certain specimens. Preferably, extraction requires less than about two minutes. Contact is generally carried out at room temperature (that is, from 18° to 25° C.), but higher temperatures up to about 40° C. may be used if desired. Preferably, extraction is carried out in a suitable extraction device which may be designed specially for that purpose. A number of such devices are shown in the art, such as in U.S. Pat. No. 4,746,614 (issued May 24, 1988 to Devaney, Jr. et al).

After suitable incubation, the solution containing extracted antigen can be neutralized with a suitable acid to reduce the pH to between 6 and 8, if desired. It may also be treated to remove endogenous peroxides. Once antigen is extracted from HSV or HSV- cells of membranes, it is desirable, although not essential, that the noted solution be prefiltered to remove cellular debris, particulate matter and other unwanted materials prior to further handling. Prefiltering can be carried out in a suitable container having a filter of some type.

A specimen containing antigen is contacted with polymeric particles to which the antigen becomes bound. This contact can occur in aqueous suspension, or the particles can be on or in a substrate (such as a microporous membrane, microtiter plate or other material known to one skilled in the art). The particles are generally water-insoluble polymeric particles prepared from polyester ionomers, polyurethanes or vinyl polymers.

The preferred polymers are prepared from hydrophobic vinyl addition monomers whose solubility in water is generally less than about 10% (w/w), such as vinyl aromatics (for example styrene and its derivatives), alkyl acrylates and methacrylates and others readily apparent to one skilled in the art. Other examples are provided hereinbelow.

These particles must have sufficient surface area per unit weight to allow sufficient antigen capture in order to provide desired assay sensitivity. Generally, this surface area is from about 0.1 to about 600, and preferably from about 0.4 to about 12, $m^2/g$ of particles. Moreover, these particles are substantially free of any chemical or biological material which would interfere with antigen binding. Particularly, the particles are free of surfactants. Antigen capture is by adsorption or covalent reaction with surface chemical groups which are part of the particles, or a combination of both. Surface groups for covalent attachment can be provided by treating particles in some manner to form the reactive moieties, or preferably, they are incorporated into the particles from the monomeric components from which the polymer is formed.

The particles can be of regular or irregular shape as long as they have the requisite surface area and can be handled in the assay in a manner such that bound antigen-antibody complex can be separated from uncomplexed materials. The shapes can be spherical, ellipsoidal, cubic or irregular. Preferably, the particles are spherical beads. Such polymeric particles are generally water-insoluble latex particles having an average particle size greater than about 0.01, and preferably from about 0.1 to about 10, micrometers.

In a preferred embodiment, the particles are prepared from polymers to which the antigen readily adsorbs upon contact, or after modest incubation at room or slightly higher temperatures. It is desired to avoid high temperature lengthy incubation which are sometimes required with materials of the prior art.

In another embodiment, the particles have surface reactive groups which covalently bind to free amine, carboxy or sulfhydryl groups on the antigen. Representative surface reactive groups include, but are not limited to, aldehyde, hydrazide, active halogen, activated 2-substituted ethylsulfonyl and vinylsulfonyl groups. Particularly useful reactive groups include active ester groups, active halogens, activated 2-substituted ethylsulfonyl and vinylsulfonyl groups with the active halogens and the activated 2-substituted ethylsulfonyl groups being most preferred.

Useful polymeric particles are prepared from one or more ethylenically unsaturated polymerizable monomers which are described below in more detail. At least one of the monomers provides the desired reactive groups on at least the surface of the particles. In some embodiments, the particles are homogeneous, that is, they are composed of the same polymer throughout. In other embodiments, the particles are composed of two or more polymers, for example as core/shell particles (as described, for example, in U.S. Pat. No. 4,997,772, (issued Mar. 5, 1991 to Sutton, Littlehale and Danielson), and in U.S. Pat. 4,401,765, issued Aug. 30, 1983 to Craig et al), or as graft copolymers as described, for example, in U.S. Pat. No. 3,700,069 (issued Oct. 24, 1972 to Tregear et al).

Monomers having an active halogen atom include vinyl chloroacetate, vinyl bromoacetate, haloalkylated vinyl aromatics (for example, chloromethylstyrene or bromomethylstyrene), haloalkyl acrylic or methacrylic esters (for example, chloroethyl methacrylate, 3-chloro-2-hydroxypropyl methacrylate and 3-chloropropyl acrylate), N-{3-[N'-(3-chloropropionyl)ureido]propyl} methacrylamide, 4-(3-chloropropionamido)styrene, 4-[N'-(3-chloropropionyl)ureido]styrene, 2-(3-chloropropionamido)ethyl methacrylate, N-[3-(3-chloropropionamido)propyl]methacrylamide, N-(3-chloroacetamidopropyl)methacrylamide, N-(2-chloroacetamidoethyl)methacrylate, 4-chloroacetamidostyrene, 4-chloroacetamidomethylstyrene, N-[3-(N'-chloroacetylureido)propyl]methacrylamide, N-[2-(N'-chloroacetylureido)ethyl]methacrylamide, 4-(N'-chloroacetylureido)styrene, m & p-(N'-chloroacetylureidomethyl)styrene, and others known to one skilled in the art. The haloalkylated vinyl aromatics, for example those having active haloalkyl groups of 1 to 3 carbon atoms, are preferred when the active halogen atom is used as the reactive group. Chloromethylstyrene is most preferred.

Representative activated 2-substituted ethylsulfonyl and vinylsulfonyl monomers can be represented by the formula (I):

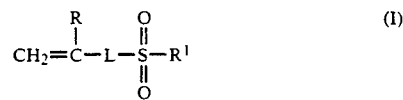

wherein R is hydrogen or substituted or unsubstituted alkyl (generally of 1 to 6 carbon atoms, such as methyl, ethyl, isopropyl or hexyl. Preferably, R is hydrogen or methyl.

$R^1$ is —CH=CHR$^2$ or —CH$_2$CH$_2$X wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is —CH$_2$CH$_2$X. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR$^3$— [wherein R$^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—),

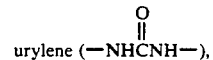

sulfonyl (—SO$_2$—), carbonate, sulfonamide, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 (issued Jul. 17, 1979 to Campbell) and 4,548,870 (issued Oct. 22, 1985 to Ogawa et al).

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art), as well as such combinations which are interrupted or terminated by one or more amide or ester groups (for example, carbonyliminoarylenealkylene). Preferably, L is substituted or unsubstituted phenylenealkylene [for example, substituted with one or more alkyl groups (as defined for R), alkoxy groups (generally of 1 to 6 carbon atoms, for example, methoxy, propoxy or butoxy) or halo groups], carbonyliminoarylenealkylene (wherein arylene and alkylene are defined above), or carbonyliminoalkyleneiminocarbonylalkylene (wherein alkylene are defined above).

Representative useful monomers include m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonylmethyl)phenyl]acrylamide, and N-[2-(2-chloroethylsulfonyl)ethylformamidomethyl]acrylamide. The first monomer is preferred.

One or more of the monomers described above can be polymerized in combination to form polymers. Preferably, one or more of them are copolymerized with at least one other ethylenically unsaturated polymerizable monomer of the hydrophobic class described herein. Generally such monomers provide various desirable properties such as hydrophobicity, dispersibility or other features. Preferred polymers can be represented by the formula (II):

—A)$_x$(B)$_y$(D)$_z$ (II)

wherein
—A— represents recurring units derived from one or more hydrophobic ethylenically unsaturated monomers,
—B— represents recurring units derived from one or more ethylenically unsaturated monomers having the requisite reactive groups described above, and
—D— represents recurring units derived from one or more ethylenically unsaturated monomers which are different than those represented by —A— or —B—.

In formula (II), x is from 0 to about 100 mole percent, y is from about 0 to 70 mole percent, and z is from 0 to about 20 mole percent. Preferably, x is from about 45 to about 100 mole percent, y is from about 0 to about 30 mole percent, and z is from 0 to about 10 mole percent.

Monomers from which the —A— recurring units are derived, both in general and in preferred embodiments, are hydrophobic and form homopolymers that are insoluble in water. Preferably, these monomers have aromatic groups. Representative hydrophobic monomers include, but are not limited to, styrene and styrene derivatives (for example, 4-vinyltoluene, 2,5-dimethylstyrene, 4-t-butylstyrene, 2-chlorostyrene and others known in the art), acrylic and methacrylic acid esters and amides (for example, n-butyl acrylate, propyl methacrylate, methyl acrylate, methyl methacrylate, ethyl methacrylate, 2-ethylhexyl methacrylate, N-phenylacrylamide and others known in the art), acrylonitrile and vinyl acetate.

The polymers can be crosslinked, if desired, in any suitable fashion. One method is to incorporate a small amount, that is up to about 10 mole percent, and preferably from about 0.3 to about 5 mole percent, of a monomer having two or more ethylenically unsaturated polymerizable groups. These monomers are included among the hydrophobic monomers from which A is derived. Representative monomers are described in *Research Disclosure*, publication 19551, Jul., 1980, page 304, and include for example, divinylbenzene, ethylene dimethacrylate, N,N'-methylenebisacrylamide, 2,2-dimethyl-1,3-propylene diacrylate, allyl acrylate, ethylidyne trimethacrylate and ethylene diacrylate. Crosslinking with such monomers, however, reduces the swellability of polymers, especially of the core of core/shell polymers caused by the organic solvent used in preferred techniques for imbibing tracer materials into polymeric particles. Therefore, crosslinking is generally limited to small amounts as required to impart water-insolubility.

Preferred monomers from which the —A— recurring units are derived are vinyl aromatic monomers, especially styrene and styrene derivatives.

The monomers from which the —B— recurring units are derived are those having the reactive groups described above.

Monomers from which the —D— recurring units are derived include monomers different than those from which —A— and —B— are derived. Specifically, the —D— recurring units are derived from monomers which impart aqueous dispersion stability to the particles or other properties. Representative monomers include, but are not limited to, anionic monomers such as sodium 2-acrylamido-2-methylpropanesulfonate, acrylic acid, methacrylic acid, 2-carboxyethyl acrylate, styrene sulfonic acid, potassium salt and m & p-carboxymethylstyrene and other ethylenically unsaturated polymerizable sulfonates, carboxylates, sulfates and phosphonates, other hydrophilic but nonionic monomers, such as 2-hydroxyethyl acrylate and 2-hydroxyethyl methacrylate and others known to one skilled in the art.

Preferred monomers from which the —D— units are derived are acrylic acid, methacrylic acid, sodium 2-acrylamido-2-methylpropanesulfonate, m & p-carboxymethylstyrene and p-styrenesulfonic acid, potassium salt.

Representative polymers of the monomers described above include the following: poly(m & p-chloromethylstyrene), poly(styrene-co-m & p-chloromethylstyrene-co-2-hydroxyethyl acrylate) (67:30:3 molar ratio), poly[styrene-co-m & p-(2-chloroethylsulfonylmethyl)styrene] (95.5:4.5 molar ratio), poly{styrene-co-N-[m & p-(2-chloroethylsulfonylmethyl)phenyl]acrylamide} (99.3:0.7 molar ratio), poly(m & p-chloromethylstyrene-co-methacrylic acid) (95:5, 98:2 and 99.8:0.2 molar ratio), poly(styrene-co-m & p-chloroethylsulfonylmethylstyrene-co-methacrylic acid) (93.5:4.5:2 molar ratio), poly{styrene-co-N-[m & p-(2-chloroethylsulfonylmethyl)phenyl]acrylamide-co-methacrylic acid} (97.3:0.7:2 molar ratio), poly(styrene-co-m & p-chloromethylstyrene) (70:30 molar ratio), poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m & p-divinylbenzene) (89:10:1 molar ratio), poly(styrene-co-2-carboxyethyl acrylate) (90:10 molar ratio), poly(methyl methacrylate-co-acrylic acid) (95:5 molar ratio), poly(styrene) and poly(styrene-co-n-butyl acrylate-co-methacrylic acid) (45:45:10 weight ratio).

The polymeric particles can be prepared using any suitable polymerization technique, including emulsion (including batch, semi-continuous and continuous), condensation and suspension polymerization techniques, graft copolymerization, and others known to one skilled in the polymer chemistry art. The method of polymerization will depend upon the type of polymer desired, whether a condensation or addition polymer. Emulsion polymerization is preferred for preparing polymers from ethylenically unsaturated polymerizable monomers as it can be used to provide particles without the use of surfactants or emulsifiers as described for example in U.S. Pat. No. 4,415,700 (noted above) and *Research Disclosure* publication 15963 (July, 1977). *Research Disclosure* is a publication available from Kenneth Mason Publications, Ltd., The Old harbourmaster's, 8 North Street, Emsworth, Hampshire PO10 7DD, England. Continuous emulsion polymerization is the most preferred technique, as described in the noted *Research Disclosure* publication. Other details of preparatory methods can be found in U.S. Pat. Nos. 4,161,407 and 4,548,870, noted above.

Staged emulsion polymerization can be used to provide a core-shell polymer composed of two different polymers. Emulsion polymerization of the core is carried to substantial completion by continuously adding reactants to a reaction vessel under standard conditions. Monomers and catalysts needed to make the shell polymer are then continuously added to the vessel containing the latex of the core polymer. In this manner, the shell has a definite known composition rather than being a mixture of core and shell monomers. Representative details of preparing the core-shell polymeric particles useful in this invention are provided in U.S. Pat. No. 4,997,772, noted above.

Almost immediately upon contact of the antigen with the particles, the antigen is bound to them. Binding occurs "directly" which means that the antigen is not bound through a linking biological compound (such as an antibody) which is attached to the support.

Then, within about 10 minutes, and preferably within about 2 minutes, of the contact, bound antigen is contacted with suitable antibody (or mixture thereof) to the Herpes simplex viral antigen so as to form an immunological complex on the support. Preferably, the assay is carried out using a disposable test device and the particles are used with a microporous membrane through which fluid and uncomplexed materials in the specimen are allowed to flow through as the antigen is bound to the particles.

Preferably, the microporous membrane is fitted into a disposable test device in which the assay can be carried out and all fluids accommodated. Useful configurations of test devices are known in the art including U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May, 1984 to Liotta). Particularly useful devices are described and claimed in E.P. Publication 280,558 (published Aug. 31, 1988) and in copending 098,248 (filed Sep. 18, 1987 by Hinckley, now abandoned). Such devices have three test wells, each well having a microporous membrane for obtaining test results as well as positive and negative control results. The membranes generally have an average pore size which allows all materials to pass through except the particles to which antigen is bound even if the particle size is less than the membrane pore size. Generally, the average pore size is from about 0.1 to about 20, and preferably from about 1 to about 10, $\mu$m. The membrane pore size is chosen so that there is maximum fluid flow through the membrane with minimum particles passing through the membrane.

The antibodies used in this assay can be polyclonal or monoclonal which can be purchased or prepared using known procedures. Preferred antibodies are monoclonal and reactive with glycoproteins from both HSV-1 and -2. One such antibody is monoclonal and is obtained using standard procedures from hybridoma cell line 283-2A1-1D4-2C3 (ATCC deposit HB-9684).

In a preferred embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with a enzyme to provide a detectable species. Where the label is an enzyme, such as glucose oxidase, urease, peroxidase, alkaline phosphatase and others, substrates and dye-providing reagents are also needed. Peroxidase and alkaline phosphatase are particularly useful.

In a particularly preferred embodiment, the label is peroxidase, and at some point in the assay, hydrogen peroxide and suitable dye-forming reagents are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In another embodiment, the HSV antibody is not labeled, and detection of the antibody-antigen complex formed and bound to the support is accomplished using a second antibody (described below) which is specific to the HSV antibody and appropriately labeled (as described above) for detection.

The antibodies used in the assay can be supplied in admixture with one or more blocking proteins which reduce nonspecific interactions on the support. Useful proteins are well known and include, for example, casein, $\alpha$-casein, fetal bovine serum and porcine gamma globulin. One useful blocking composition comprises a nonimmunological blocking protein and an amphoteric surfactant.

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with a buffered wash solution, such as a phosphate buffer or a buffered solution of a nonionic surfactant. A particularly useful wash solution has a high pH and advantageously lowers background of the assay. Such washing is used advantageously to separate uncomplexed materials and specimen debris and fluid from the complex bound to the particles. Preferably, the uncomplexed materials are washed through the microporous membrane described herein.

In the embodiment described above where the HSV antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures after a suitable time.

Where the HSV antibody is unlabeled, after washing the bound complex, it is contacted with an antibody directed to the unlabeled antibody. This second antibody (that is an anti-antibody) is appropriately labeled with any of the labels described above, and can be supplied with a blocking composition as described above. The antibody can be monoclonal or polyclonal and either purchased or prepared using known techniques.

After this contact, the resulting antigen-antibody-antibody complex which is bound to the particles is incubated for up to about 10 minutes at a temperature of from about 15° to about 30°0 C. Preferably, the incubation is at room temperature for up to about 5 minutes.

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The diagnostic kit of this invention comprising at least the following components:
a. polymeric particles which have a surface area of from about 0.1 to about 600 m$^2$/g of particles, which particles are capable of having herpes simplex viral antigen bound thereto,
b. a disposable test device comprising a microporous membrane which has an average pore size which prevents the particles having antigen bound thereto from passing through the membrane, and
c. antibodies directed to herpes simplex viral antigen.

The kit can optionally include other materials including wash solutions, extraction compositions, enzyme substrates or dye-providing compositions, anti-antibody compositions, pipettes, test tubes, instructions or other reagents and equipment normally used in performing the assays.

The particles can be supplied in the kit as a powder, but preferably they are in an aqueous suspension which contains suitable buffers or dispersing agents.

The following materials, compositions and solutions were used in the examples below, which examples are provided to illustrate, but not limit the scope of, the present invention.

Antibody Preparation

Hybridoma cells producing monoclonal antibodies to herpes simplex virus were prepared using known procedures described by Köhler et al (*Nature*, 256, pp. 495–497, 1975). A hybridoma cell line was generated which produced a monoclonal antibody reactive to an epitope on a glycoprotein antigen common to both HSV-1 and HSV-2. The hybridoma cell line has been deposited as ATCC HB-9684.

Antigen Preparation

To prepare the antigen for use as the positive control, HSV-1 strain F and HSV-2 strain G were grown separately in HEP-2 cells (ATCC CCL-23). The infected cells were pelleted by low speed centrifugation, and the pellets were resuspended to a volume of 15 ml in phosphate buffered saline in a 50 ml Corex tube. The resuspended cells were sonicated, exposed to aminomethyltrioxsalen (500 mg/ml) for 15 minutes, followed by ultraviolet irradiation for 15 minutes under constant stirring.

The positive control well of the test devices contained HSV-1 and HSV-2 antigens (UV inactivated and detergent lysed), incorporated on the filter membrane of the test well in admixture with bovine serum albumin (0.1 weight %) and a hydrophilic polymer (5 weight %).

Antibody Conjugate Preparation

Monoclonal antibodies to herpes simplex virus were conjugated to horseradish peroxidase (Miles Laboratories) using the method described by Yoshitake et al, *Eur. J. Biochem.*, 101, 395 (1979). The resulting conjugate was mixed with a blocking composition containing α-casein (0.5 weight %, Sigma Chemical Co.), TWEEN 20 nonionic surfactant (0.1 weight %, Sigma Chemical), thimerosal preservative (0.01 weight %) and p-methoxyphenol (100 mmolar), then sterile filtered. The final antibody concentration in this solution was 1.5 μg/ml. It was stored with bovine serum albumin (1 weight %).

Leuco Dye-Providing Composition

This composition contained hydrogen peroxide (10 mmolar), 2-(4-hydroxy-3-methoxyphenyl)-4,5-bis(4-methoxyphenyl)imidazole leuco dye (0.005 weight %), poly(vinylpyrrolidone) (1 weight %), 4'-hydroxyacetanilide (5 mmolar) and diethylenetriaminepentaacetic acid (10 mmolar).

Wash Solution

An aqueous wash solution was prepared containing TRITON™ X-100 nonionic surfactant (0.1 weight %), ethanolamine hydrochloride (0.26 molar, Sigma Chemical) and preservative (0.01 weight %), with the pH adjusted to 10.75 with 12 normal sodium hydroxide.

Extraction Composition

An extraction composition was prepared by mixing the following components in water: NONIDET NP-40 nonionic surfactant (5 weight %, tradename of Sigma Chemical), sodium deoxycholate (0.2 weight %, Sigma Chemical), ethanolamine hydrochloride (0.26 molar), and sodium dodecyl sulfate anionic surfactant (0.1 weight %). The pH of the composition was adjusted to 9 with 12 normal sodium hydroxide.

Phosphate Buffered Saline Solution

This solution (0.05 molar) was prepared from sodium chloride (0.15 molar), sodium dihydrogen phosphate (0.01 molar) and sodium hydrogen phosphate (pH 7.2, 0.04 molar).

Blocking Composition

An aqueous blocking composition was prepared comprising α-casein (0.5 weight %), TWEEN 20 (tradename, 0.1 weight %), p-methoxyphenol (100 mmolar) and preservative (0.01 weight %).

A disposable test device, having three test wells and similar to that described in copending U.S. Ser. No. 98,248 (noted above), was used in the assay. The test devices had uncoated nylon microporous membranes BIODYNE™ A from Pall Corp.) in each test well.

Preparation of Polymeric Particles

The three solutions outlined below were continuously added to a 1365 ml vessel containing deoxygenated water at 80° C. at the indicated rates:

Solution 1: Styrene (739 g), m & p-(2-chloroethylsulfonylmethyl)styrene (82 g) and 1-dodecanethiol (8.2 g) at 2.5 g/min. for 380 minutes.

Solution 2: Ammonium persulfate (19.7 g) and distilled, deoxygenated water (1152 g) at 2.14 g/min. for 380 minutes.

Solution 3: Sodium metabisulfite (9.9 g) and distilled water (1152 g) at 2.27 g/min. for 380 minutes.

After 380 minutes, the reaction was stopped, yielding about 1218 g of latex at 33.4% solids. The latex was dialyzed for 3 days to yield a latex having 27.3% solids and a pH of 5. This latex was diluted to 13.5% solids. NMR analysis confirmed a 96:4 molar ratio of styrene to the second monomer. The resulting latex particles of poly[styrene-co-m & p-(2-chloroethylsulfonylmethyl)styrene] (95.5:4.5 molar ratio) had an average diameter (and surface area) of about 2.1 μm (2.86 m$^2$/g) as measured by transmission electron microscopy.

Polystyrene, poly(styrene-co-n-butyl acrylate) (83:17 molar ratio) and poly(styrene-co-m & p-chloromethylstyrene) (77:23) were similarly prepared and had average diameters (and surface area, m$^2$/g) of 1.6 (3.75), 2.5 (2.40) and 1.9 (3.15) μm, respectively.

EXAMPLES 1-4

Assays for Herpes Simplex Virus

These examples demonstrate the practice of this invention using four different polymeric particles for binding extracted herpes simplex viral antigen in assays.

Test samples containing HSV antigen were prepared mixing HSV cell lysate (described above, 4 μl) which had been diluted 1:80 in phosphate buffered saline solution (containing 0.1 mg/ml bovine serum albumin) in additional phosphate buffered saline solution (64 μl). Phosphate buffered saline solution alone was used as a Control sample (68 μl).

Both test and Control samples were mixed with the extraction composition (932 μl) for 5 minutes at room temperature. The final antigen dilution added to the test wells was 1:20,000. All three test wells of the disposable test devices were used in the assays. The test and Control samples were prefiltered through a 10 μm filter which had been coated with a nonionic surfactant, then added to the test wells of test devices containing a nylon microporous membrane. HSV antigen was immediately bound to the membrane.

The test wells were washed with the wash solution noted above (200 μl), followed by addition of a hydrogen peroxide solution (120 μl of a 5% solution). A second washing (200 μl) was carried out.

The peroxidase labeled anti-HSV conjugate (40 μl) was added in a blocking solution to the test wells, followed by incubation for 5 minutes at room temperature. After two washings (each with 200 μl), the leuco dye providing composition (80 μl) was added to each well. After another 5 minutes incubation at room temperature, the dye forming reaction was stopped by adding sodium azide (0.1 weight %), and the resulting dye density on each membrane was determined by density transmittance ($D_T$).

This procedure was also followed using polymeric particles for antigen binding. The particles used were as follows:

Example 1: poly(styrene-co-m & p-chloromethylstyrene),

Example 2: poly(styrene),

Example 3: poly(styrene-co-n-butyl acrylate), and

Example 4: poly[styrene-co-m & p-(2-chloroethylsulfonylmethyl)styrene].

An aqueous suspension (0.2 weight %) of the particles were added to the test wells of test devices before extracted antigen was added, and the assay then carried out as described above.

The results of these assays are shown in the Figure, and indicate that improved sensitivity was obtained using particles for antigen binding as compared to membrane binding alone (Control).

The invention has been described in detail with particular reference to preferred embodiments thereof, but it will be understood that variations and modifications can be effected within the spirit and scope of the invention.

We claim:

1. A method for the determination of a herpes simplex virus comprising:
   A. contacting a specimen suspected of containing herpes simplex viral antigen with polymeric particles which have a surface area of from about 0.1 to about 600 m$^2$/g of particles, each particle being substantially free of any chemical or biological material and having an average diameter of from about 0.01 to about 10 micrometers, which particles are capable of having herpes simplex viral antigen bound directly thereto,
   B. within about 10 minutes of contacting step A, contacting herpes simplex viral antigen directly bound to said particles with herpes simplex viral antibody so as to form an immunological complex on said particles,
   C. separating said bound complex from uncomplexed herpes simplex viral antibody using a microporous membrane having an average pore size of from about 0.1 to about 20 μm, and
   D. determining the presence of said complex as a measure of the presence of herpes simplex virus in said specimen, said method being carried out within about 30 minutes.

2. The method of claim 1 wherein said bound complex is separated from uncomplexed materials using a microporous membrane in a disposable test device.

3. The method of claim 1 wherein said herpes simplex viral antibodies are labeled for detection.

4. The method of claim 3 wherein said herpes simplex viral antibodies are labeled with an enzyme, and said complex is determined using a dye-providing composition which comprises a substrate for said enzyme.

5. The method of claim 1 wherein said herpes simplex viral antibodies are unlabeled, and said immunological complex is determined using an enzyme-labeled antibody which binds to said herpes simplex viral antibody.

6. The method of claim 1 wherein said particles are composed of a polymer prepared from hydrophobic ethylenically unsaturated addition monomers.

7. The method of claim 1 wherein said polymeric particles have surface groups which are capable of covalently reacting with said herpes simplex viral antigen.

8. The method of claim 7 wherein said surface groups are selected from the group consisting of active halogens, activated 2-substituted ethylsulfonyl and vinylsulfonyl groups.

9. A method for the determination of herpes simplex virus comprising:
   A. extracting antigen from herpes simplex virus in a biological specimen,
   B. contacting said extracted antigen with polymeric particles which have a surface area of from about 0.1 to about 600 m²/g of particles, each particle being substantially free of surfactant or any biological material and having an average diameter of from about 0.01 to about 10 micrometers, which particles are capable of having herpes simplex viral antigen directly bound thereto, said particles being in association with a microporous membrane which has an average pore size of from about 0.1 to about 20 μm,
   C. within about 2 minutes of said contacting step A, contacting herpes simplex viral antigen directly bound to said particles with herpes simplex viral antibody so as to form an immunological complex on said particles,
   D. separating said bound complex from uncomplexed herpes simplex viral antibody by washing uncomplexed herpes simplex viral antibody through said membrane, and
   E. determining the presence of said complex as a measure of the presence of herpes simplex virus in said specimen,
   said method being carried out within about 30 minutes.

10. The method of claim 9 wherein said herpes simplex viral antibodies are labeled for detection.

11. The method of claim 10 wherein said herpes simplex viral antibodies are labeled with an enzyme, and said complex is determined using a dye-providing composition which comprises a substrate for said enzyme.

12. The method of claim 11 wherein said enzyme is peroxidase, and said dye-providing composition comprises a leuco dye which provides a dye in the presence of peroxidase and hydrogen peroxide.

13. The method of claim 9 wherein said herpes simplex viral antibodies are unlabeled, and said bound complex is detected by contacting it with anti-antibodies which bind to said herpes simplex viral antibodies, and said anti-antibodies being enzyme labeled.

14. The method of claim 9 wherein said polymeric particles have surface groups which are capable of covalently reacting with said Herpes simplex viral antigen.

15. The method of claim 14 wherein said surface groups are selected from the group consisting of active halogens, activated 2-substituted ethylsulfonyl and vinylsulfonyl groups.

16. A diagnostic kit useful for the determination of herpes simplex virus comprising:
   a. polymeric particles which are substantially free of chemical or biological materials, having an average diameter of from about 0.01 to about 10 micrometers, and which have a surface area of from about 0.1 to about 600 m²/g of particles, which particles are capable of having herpes simplex viral antigen directly bound thereto,
   b. a disposable test device comprising a microporous membrane which has an average pore size of from about 0.1 to about 20 μm, and
   c. antibodies which bind to herpes simplex viral antigen.

17. The kit of claim 16 wherein said antibodies are enzyme labeled.

18. The kit of claim 16 wherein said antibodies are unlabeled, and said kit further comprises labeled antibodies which bind to said herpes simplex viral antibodies.

19. The kit of claim 16 wherein said test device comprises three test wells, each well having a microporous membrane prepared from a polyamide mounted therein.

20. The kit of claim 16 wherein said polymeric particles are supplied on the microporous membrane of said test device.

21. The kit of claim 16 wherein said polymeric particles are supplied in an aqueous suspension.

* * * * *